United States Patent [19]

Jessel, Jr. et al.

[11] Plant 5,019

[45] Mar. 29, 1983

[54] CHRYSANTHEMUM PLANT

[75] Inventors: Walter H. Jessel, Jr., Fremont; William E. Duffett, Salinas, both of Calif.

[73] Assignee: Yoder Brothers, Inc., Barberton, Ohio

[21] Appl. No.: 313,274

[22] Filed: Oct. 21, 1981

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant known by the cultivar name Cymbals and particularly characterized as to uniqueness by the combined characteristics of flat capitulum form, with excellent form retention; single capitulum type; golden bronze ray floret color; diameter across face of capitulum ranging from 125 to 140 mm. at maturity; uniform nine week photoperiodic flowering response to short days; medium plant height when grown as a pinched disbud pot; and upright branching pattern.

3 Drawing Figures

The present invention comprises a new and distinct cultivar of *Chrysanthemum morifolium*, Ramat., hereinafter referred to by the cultivar name Cymbals.

Cymbals is a product of a planned breeding program which had the objective of creating new chrysanthemum cultivars for pinched disbudded pot mum programs, having single capitulum type, golden bronze ray floret color, nine week flowering response and having the ability to produce commercially acceptable quality in year round programs. Such traits in combination were not present in previously available commercial cultivars.

Cymbals was originated from a cross made in a controlled breeding program in Barberton, Ohio in 1974. The female parent was an unnamed yellow single originated from a cross between Red Rover (unpatented) and an unnamed seedling.

The male parent of Cymbals was an unnamed yellow single originated from a cross between two unnamed seedlings.

Cymbals was discovered and selected as one flowering plant within the progeny of the stated cross by William E. Duffett and Walter H. Jessel, Jr. on Dec. 3, 1975 in a controlled environment in Barberton, Ohio.

The first act of asexual reproduction of Cymbals was accomplished when vegetative cuttings were taken from the initial selection in February, 1976 in a controlled environment in Barberton, Ohio by a technician working under formulations established and supervised by William E. Duffett. Horticultural examination of selected units initiated Nov. 22, 1978 has demonstrated that the combination of characteristics as herein disclosed for Cymbals are firmly fixed and are retained through successive generations of asexual reproduction.

Cymbals has not been observed under all possible environmental conditions. The phenotype may vary significantly with variations in environment such as temperature, light intensity and day length. The observations, measurements and comparisons describe plants grown in Salinas, Calif. under greenhouse conditions which approximate those generally used in commercial practice.

The following traits have been repeatedly observed and are determined to be basic characteristics of Cymbals which in combination distinguish this chrysanthemum as a new and distinct cultivar:

(1) flat capitulum form, with excellent form retention;

(2) single capitulum type;

(3) golden bronze ray floret color, with minimal color oxidation;

(4) diameter across face of capitulum ranging from 125 to 140 mm. at maturity;

(5) uniform nine week photoperiodic flowering response to short days;

(6) medium plant height (requiring 1-2 long day weeks prior to pinch and short days, and one application 2500 ppm B-9 SP, 14 to 21 days after the beginning of short days to attain a flowered plant height of 25 to 40 cm.); and (7) upright branching pattern.

The accompanying photographic drawings show typical inflorescence and foliage characteristics of Cymbals, with the colors being as nearly true as possible with illustrations of this type. Sheet 1 is a color photograph of a flowering plant of Cymbals. Sheet 2 is a black and white photograph showing three views of the inflorescence of Cymbals. Sheet 3 is a black and white photograph showing the foliage of Cymbals at three stages of growth.

Of the many commercial cultivars known to the present inventors, the most similar in comparison to Cymbals is Improved Yellow Marguerita (unpatented; commercially available).

Reference is made to attached chart A which compares certain characteristics of Cymbals to those same characteristics of Improved Yellow Marguerita.

In the following description, color references are made to The Royal Horticultural Color Chart. The color values were determined between 9:00 A.M. and 10:00 A.M. on Sept. 9, 1981 under 120 foot-candle light intensity at Salinas, Calif.

Classification:

*Botanical.*—*Chrysanthemum morifolium*, Ramat., cv. Cymbals.

*Commercial.*—Pinched disbud pot.

I. INFLORESCENCE (See sheets 1 and 2)

A. Capitulum:

*Form.*—Flat.

*Type.*—Single.

*Daimeter across face.*—125 to 140 mm.

B. Corolla of ray florets:

*General tonality from a distance of* 3 *meters.*—14A.

*Color (abaxial).*—16B oxidizing to 12A.

*Color (adaxial).*—9C.

C. Corolla of disc florets:

*Color (immature).*—Approximately 144B.

*Color (mature).*—Approximately 14A.

*Persistence.*—Resists shatter.

D. Reproductive organs:

*Androecium.*—Present disc florets only; scant to few; scant pollen.

*Gynoecium.*—Present both ray and disc florets.

II. PLANT

A. General appearance:

*Height.*—Medium 25 to 40 cm.

*Branching pattern.*—Upright.

B. Foliage:

*Color (abaxial).*—137A.

*Color (adaxial).*—137C.

*Shape.*—Moderately lobed and slightly serrated.

CHART A

COMPARISON OF CYMBALS AND IMPROVED YELLOW MARGUERITA

| | RAY | CAPITULUM |
|---|---|---|

CHART A-continued

COMPARISON OF CYMBALS AND IMPROVED YELLOW MARGUERITA

| CULTIVAR | FLORET COLOR | FORM AND TYPE | BRANCHING PATTERN |
|---|---|---|---|
| CYMBALS | Golden Bronze | Flat Single | Upright |
| IMPROVED YELLOW MARGUERITA | Yellow | Flat Single | Upright |

| CULTIVAR | DIAMETER ACROSS FACE OF CAPITULUM | PLANT HEIGHT | FLOWERING RESPONSE PERIOD |
|---|---|---|---|
| CYMBALS | 125 to 140 mm. | Medium 25 to 40 cm. | 9 week |
| IMPROVED YELLOW MARGUERITA | 130 to 150 mm. | Tall 30 to 50 cm. | 9 week |

COMPARISONS MADE OF PLANTS GROWN AS PINCHED DISBUDDED POTS IN SALINAS, CALIFORNIA.

We claim:

1. A new and distinct cultivar of *Chrysanthemum morifolium,* Ramat., plant known by the cultivar name of Cymbals, as described and illustrated, and particularly characterized as to uniqueness by the combined characteristics of flat capitulum form, with excellent form retention; single capitulum type; golden bronze ray floret color, with minimal color oxidation; diameter across face of capitulum ranging from 125 to 140 mm. at maturity; uniform nine week flowering response; medium plant height; and upright branching pattern.

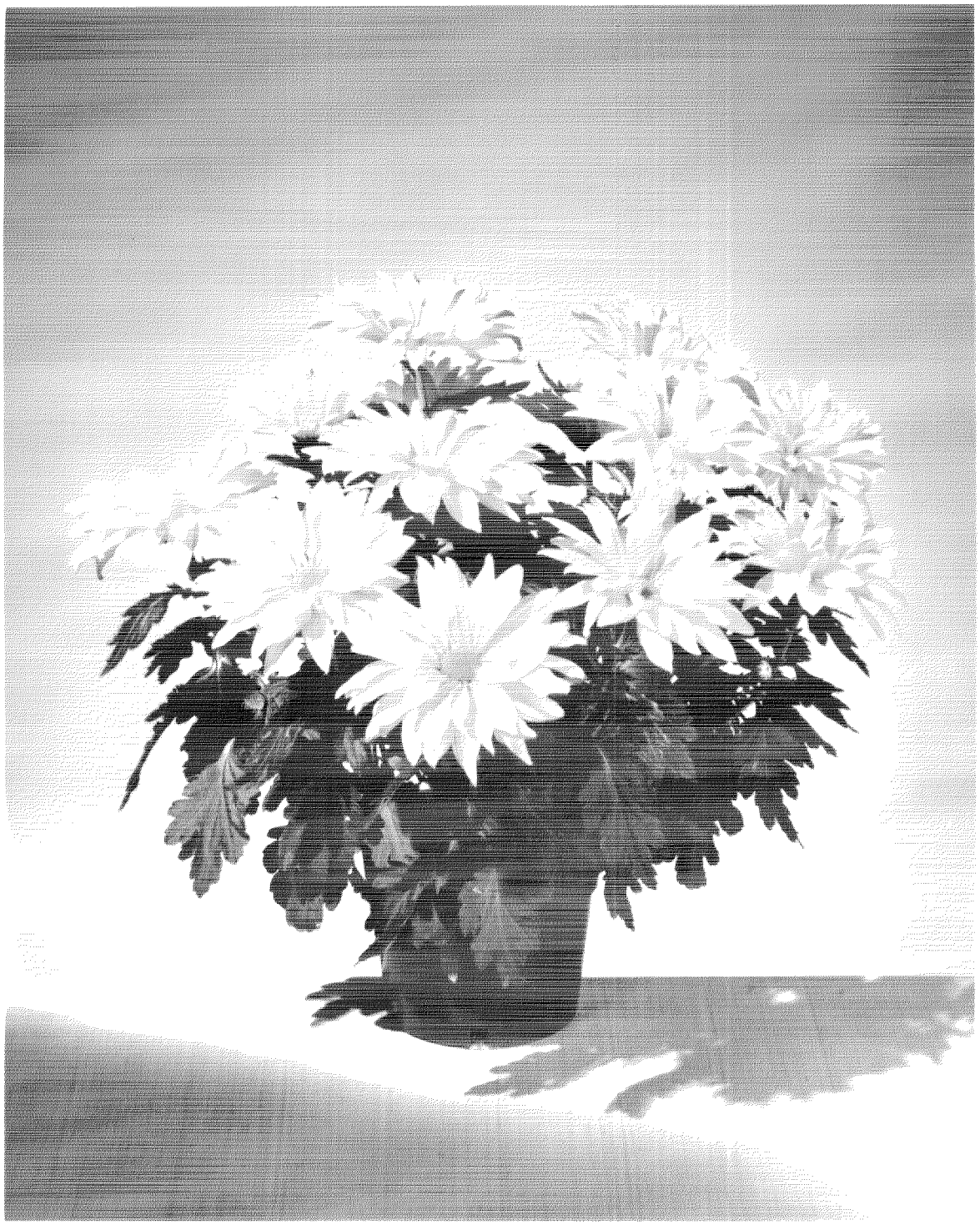

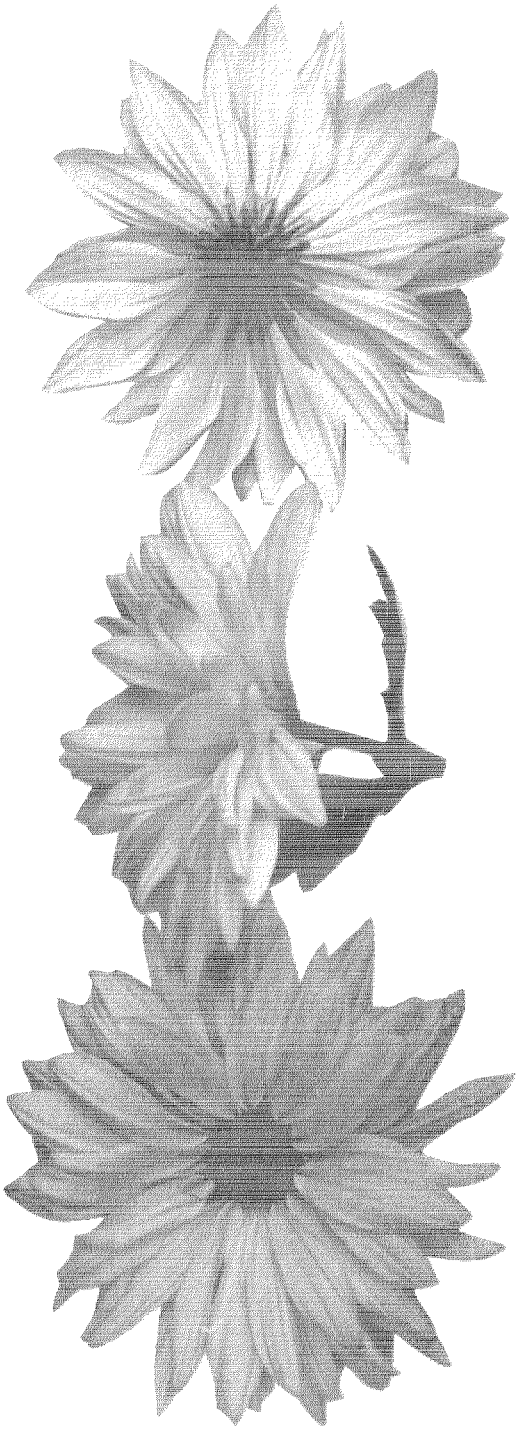

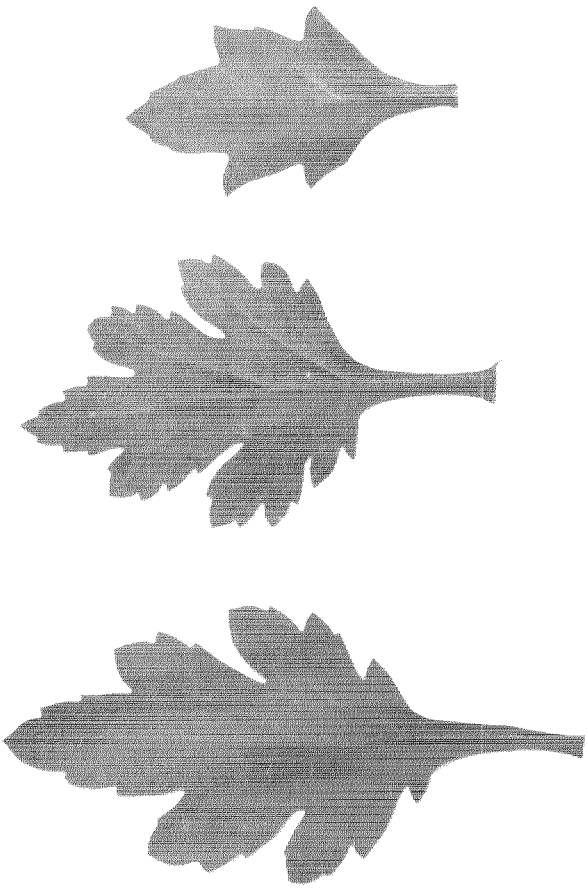

* * * * *